United States Patent [19]

Hewitt et al.

[11] Patent Number: 5,364,358
[45] Date of Patent: Nov. 15, 1994

[54] DEVICE FOR CONTROLLING THE INFLATION OF A BALLOON CATHETER

[75] Inventors: Geoffrey A. Hewitt, Dundas; Andrew K. Rath; Harvey K. McQuarrie, both of Kitchener, all of Canada

[73] Assignee: Cardio-Search Limited, Dundas, Canada

[21] Appl. No.: 787,888

[22] Filed: Nov. 5, 1991

[51] Int. Cl.⁵ ............................................. A61M 29/00
[52] U.S. Cl. ................................ 604/99; 604/97; 604/100; 604/212; 604/216; 604/217
[58] Field of Search ............................. 604/97–100, 604/211, 212, 214, 216, 217, 118, 142, 146, 37

[56] References Cited

U.S. PATENT DOCUMENTS

| | | |
|---|---|---|
| 2,544,847 | 3/1951 | Malesky . |
| 2,922,174 | 1/1960 | Mathews . |
| 3,154,078 | 10/1964 | Goodrich, Jr. ................. 604/97 |
| 3,176,691 | 4/1965 | Ericson ......................... 604/214 |
| 3,360,818 | 1/1968 | Edwards . |
| 3,445,878 | 5/1969 | Stephens . |
| 3,634,924 | 1/1972 | Blake et al. . |
| 3,746,003 | 7/1973 | Blake et al. . |
| 3,995,623 | 12/1976 | Blake et al. . |
| 4,159,722 | 7/1979 | Walker . |
| 4,207,891 | 6/1980 | Bolduc ........................... 604/97 |
| 4,227,534 | 10/1980 | LaRosa . |
| 4,370,982 | 2/1983 | Reilly ............................. 604/99 |
| 4,583,917 | 4/1986 | Shah .............................. 604/99 |
| 4,583,974 | 4/1986 | Kokernak ..................... 604/99 |
| 4,598,707 | 7/1986 | Agdanowski et al. ........ 604/100 |
| 4,654,027 | 3/1987 | Dragan et al. ................ 604/99 |
| 4,692,157 | 9/1987 | Landau et al. ................ 604/214 |
| 4,743,230 | 5/1988 | Nordquest .................... 604/99 |
| 4,762,125 | 8/1988 | Leiman et al. . |
| 4,793,351 | 12/1988 | Landman et al. ............ 604/99 |
| 4,832,692 | 5/1989 | Box et al. ..................... 604/99 |
| 4,838,864 | 6/1989 | Peterson ....................... 604/100 |
| 4,919,121 | 4/1990 | Rydell et al. ................. 604/99 |
| 5,015,233 | 5/1991 | McGough et al. ........... 604/97 |
| 5,137,514 | 8/1992 | Ryan ............................. 604/211 |
| 5,147,300 | 9/1992 | Robinson et al. ............ 604/97 |
| 5,168,757 | 12/1992 | Rabenau et al. ............. 604/99 |
| 5,209,732 | 5/1993 | Lampropoulous et al. .. 604/98 |
| 5,215,523 | 6/1993 | Williams et al. ............. 604/97 |

FOREIGN PATENT DOCUMENTS

| | | | |
|---|---|---|---|
| 0861659 | 2/1961 | United Kingdom .......... | 604/37 |
| 9000072 | 1/1990 | WIPO ........................... | 604/216 |

OTHER PUBLICATIONS

"Measurement of cardiac output by thermal dilution in man", Jrnl. of Applied Physiology, vol. 24, No. 3, Mar. 1968, pp. 434–438.

"Thermodilution cardiac output determination with a single flow-directed catheter", American Heart Jrnl., vol. S3, No. 3 Mar. 1972, pp. 306–311.

"Measurement of Blood Flow by Thermodilution", Seminar on Clinical Application of Techniques to Measure Blood Flow in Man, Part II, The Amer. Jrnl. of Cardiology, vol. 29, Feb. 1972 pp. 241–246.

"Catherization of the Heart in Man with Use of a Flow-Directed Ballon-Tipped Catheter", The New England Jrnl. of Med., vol. 283, No. 9, Aug. 27, 1970, pp. 447–451.

"A New Technique for Measurement of Cardiac Output by Thermodilution in Man", The Amer. Jrnl. of Cardiology, vol. 27, Apr. 1971, pp. 392–396.

Instruction sheet for the Swan-Ganz Flow-Directed Thermodilution Catheter bearing the copyright notice to Edwards Lab. of 1974 and a publication date of Aug. 1974.

*Primary Examiner*—C. Fred Rosenbaum
*Assistant Examiner*—Ron Stright, Jr.
*Attorney, Agent, or Firm*—Keck, Mahin & Cate

[57] ABSTRACT

A device for controlling the inflation of a balloon catheter includes a variable volume chamber and an actuator to expel air from the chamber. Movement of the actuator is inhibited by a releasable latch to prevent unintentional inflation of the catheter. An adjustable abutment limits movement of the actuator after the latch is released to prevent overinflation of the balloon.

17 Claims, 6 Drawing Sheets

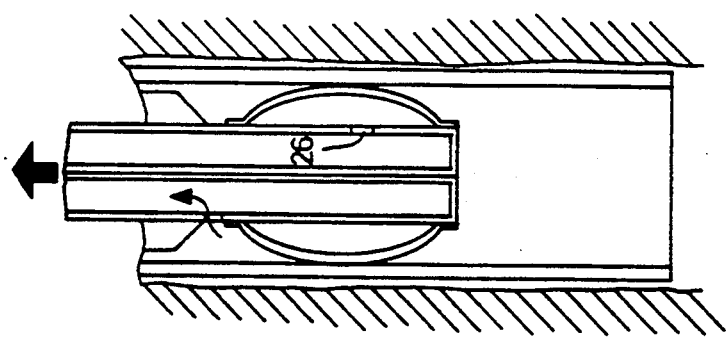
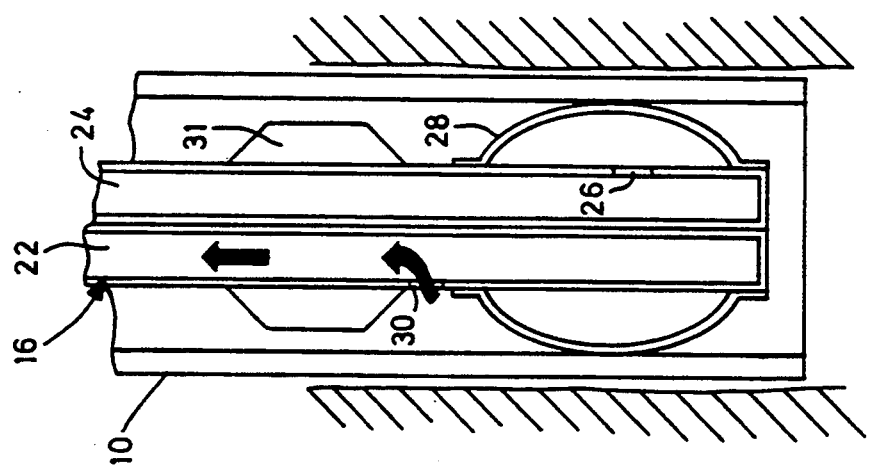

DEVICE FOR CONTROLLING THE INFLATION OF A BALLOON CATHETER

FIELD OF THE INVENTION

The present invention relates to devices to control the inflation of a balloon catheter

BACKGROUND AND SUMMARY OF THE INVENTION

It is a common practice to insert tubes into a patient to convey fluids to or discharge fluids from the patient. These procedures facilitate recovery of the patient but may at the same time lead to complications due to the environment in which they operate.

One such environment is when a respiratory tube is inserted through the pharynx and larynx into the lungs of a patient. This tube conveys oxygen with a relatively high humidity to the lungs which produces a very humid atmosphere within the lungs and within the tube. The high moisture content allows secretions to be deposited on the wall of the tubes and if left unattended leads to secondary infections. Normally an attempt is made to remove the secretions by inserting a suction tube into the endotrachial tube. However, when such a tube is inserted, only a small portion of the secretions is removed so that the cleaning is ineffectual, Moreover, the procedure is relatively long, leading to restriction in the cross-section of the tube and some discomfort to the patient during the procedure.

The secretions also significantly reduce the cross-sectional area of the tube, increasing the resistance to fluid flow in the tube.

An attempt to use a mechanical device such as a scraper or swab to clean the tube would face similar problems in that the secretions may be dislodged into the patient's lungs.

A balloon catheter is an elongate tube having a plurality of radial passages through the wall of the tube usually at one end. A membrane surrounds the passages so that upon introduction of pressure into the tube, the membrane is inflated. The catheters may be used in a variety of applications where it is desirable to seal one part of a tubular passage from another. For example, the catheter might be inserted into a blood vessel to isolate a portion of the blood vessel while plaque or the like is removed. Frequently such catheters are utilized with two lumens, one of which is used to inflate the membrane and the other of which can be used to extract materials from within the vessel.

Particular care must be taken when using balloon catheters, as overinflation could cause damage to the vessel against which the balloon engages, or alternatively cause damage of the catheter with serious consequences. Moreover, care must also be taken during insertion and extraction of the catheter to ensure that it does not unintentionally inflate or deflate. There is therefore a need for a device to control the inflation and deflation of a catheter.

It has now been recognized that a balloon catheter may offer a solution to the cleaning of such tubes provided appropriate control can be exercised when using the catheter.

Within the context of cleaning an ETT, overinflation of the catheter may cause it to bind on the walls of the tube and so inhibit its extraction. Likewise, unintentional inflation of the catheter during insertion may push secretions into the lung rather than removing them as the catheter is extracted.

It is therefore an object of the present invention to provide a device for controlling the inflation of a balloon catheter to permit its use in a number of environments and to provide a method of using such a catheter in the cleaning of tubes.

According therefore to one aspect of the present invention, there is provided a device to control the inflation of a balloon catheter comprising;
   a variable volume chamber having an outlet for connection to a lumen of a balloon catheter,
   an actuator movable relative to the chamber to vary the volume of the chamber and expel air therefrom to inflate said balloon,
   a releasable latch operable to inhibit movement of the actuator relative to the chamber; and
   an abutment to limit movement of the actuator upon release of the latch to thereby limit the volume of air expelled from the chamber to inflate the catheter, said abutment being adjustable relative to the actuator to vary the volume of air expelled.

The device of the present invention provides for a controlled inflation and prevents unintentional inflation of the catheter. It has been recognized that this device makes it possible to insert a balloon catheter into a tube in a deflated condition, inflate the catheter and extract it from the tube to wipe the surfaces of the tube and remove secretions. Thus the device may be used in combination with a catheter as a method of cleaning such tubes.

According therefore to a further aspect of the present invention, there is provided a method of wiping the inner wall of a tube comprising the steps of inserting into the tube in a deflated condition a balloon catheter, inhibiting inflation of the catheter until a predetermined location has been attained, subsequently inflating said catheter to engage said inner wall with a force to permit relative movement between the wall and the catheter and withdrawing said catheter from said tube while inhibiting further inflation.

BRIEF DESCRIPTION OF THE DRAWINGS

An embodiment of the invention will now be described by way of example only with reference to the accompanying drawings, in which.

DETAILED DESCRIPTION OF THE INVENTION

Figure 1:
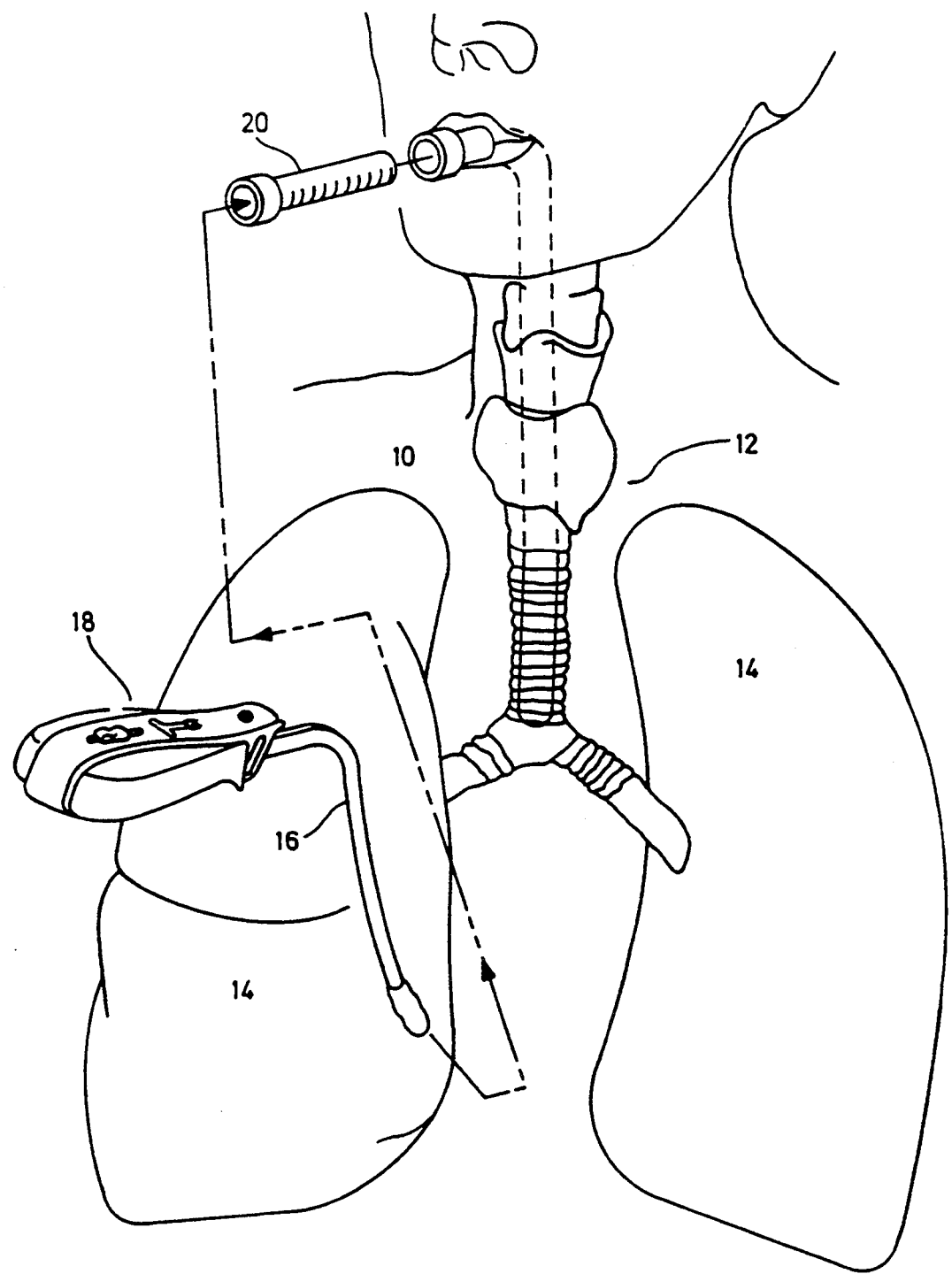
FIG. 1 is a schematic representation of the environment in which the device is to be used showing an ETT and a catheter to be inserted into that tube.

Referring therefore to FIG. 1, an ETT 10 has been inserted through the larynx and pharynx 12 of a patient for connection to a ventilator to supply air to the lungs indicated at 14. The ETT 10 is a standard medical tube of a predetermined length and diameter and made from a suitable non-invasive material compatible with the human body.

To effect cleaning of the tube 10 and remove secretions therefrom, a dual lumen catheter 16 is assembled with an inflation device 18 and inserted through a tubular spacer 20 into tube 10. As shown more fully in FIGS. 6b through 6d, the catheter 16 includes a pair of lumens 22,24. The lumen 24 is provided with radial passages 26 which are surrounded by a flexible membrane 28 that is sealed to the lumen walls above and below the radial passages 26.

The lumen 22 is also provided with a radial passage 30 located above the membrane 28 that allows movement of fluids into and out of the lumen 22.

A series of radial vanes 31 are located on the catheter 16 adjacent membrane 28. Vanes 31 act to centralize the catheter and minimize contact with the inner walls of the tube during insertion.

Figure 6A:
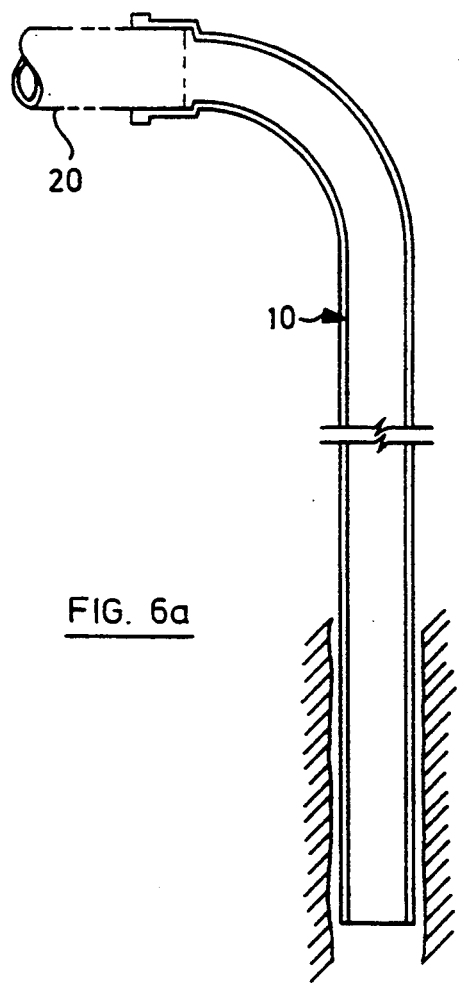
FIG. 6 is a schematic representation showing the stages of using the device with FIG. 6a showing a section through the tube into which the catheter is to be inserted, FIG. 6b showing the catheter as it is inserted, FIG. 6c showing use of the catheter after inflation.
FIG. 6d showing removal of the catheter in an inflated condition.

The supply of pressure through the lumen 24 inflates the membrane as shown in FIG. 6c to cause it to engage the walls of the tube 10. The membrane 28 is made from a flexible material such as latex, silicone, or polyvinylcholoride in a well-known manner and will not be described further.

The surface of the membrane 28 is preferably formed with a porous fabric covering to enhance the wiping action of the membrane 28 against the inner wall of tube 10.

Such a covering may also be useful in absorbing a portion of the secretions or could be used to carry a biocompatible bacteria inhibiting solution or gel, e.g. an antibiotic, and deposit it on the walls on the tube 10.

Figure 2:
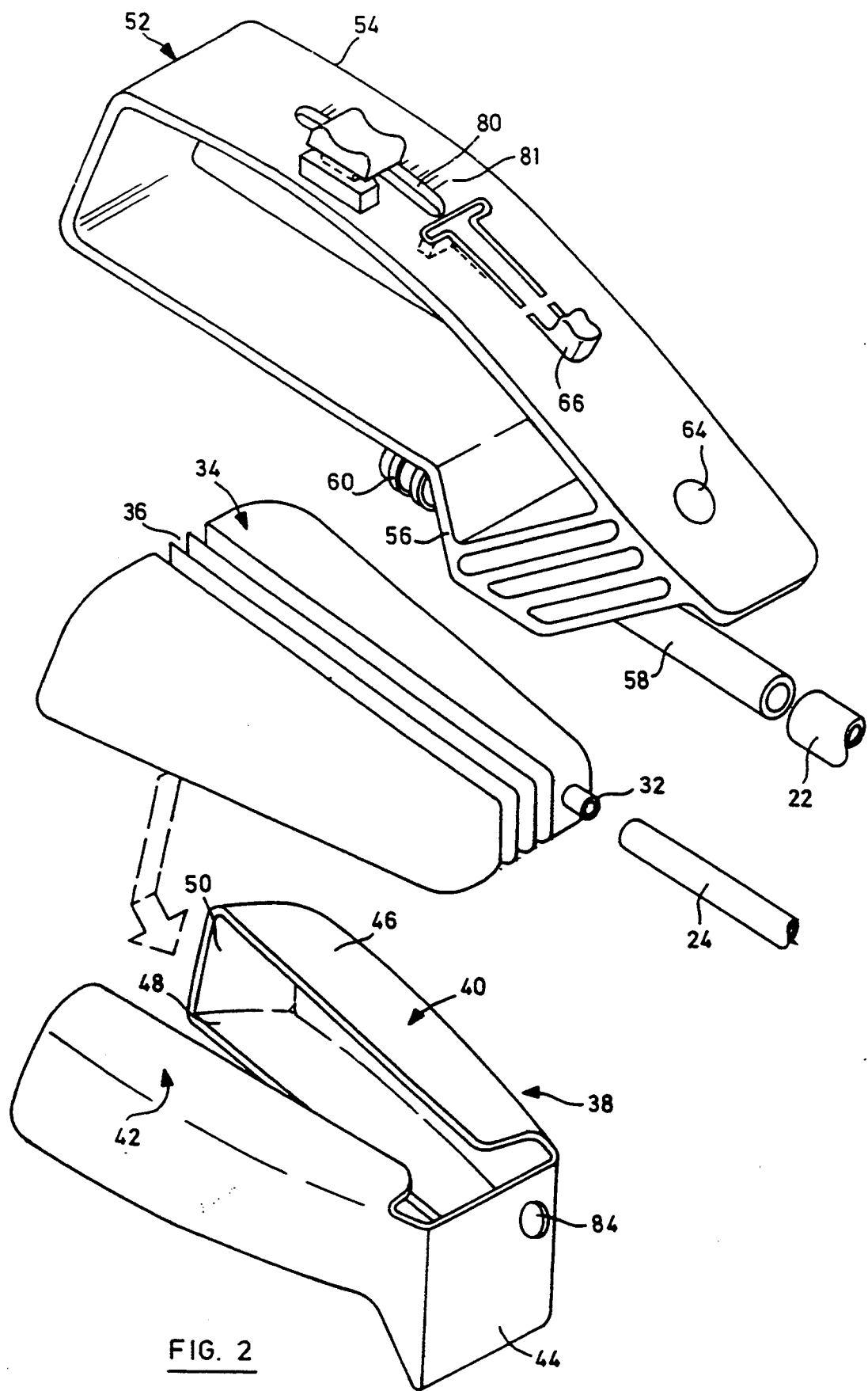
FIG. 2 is an exploded view of the device shown in FIG. 1.
Figure 3:
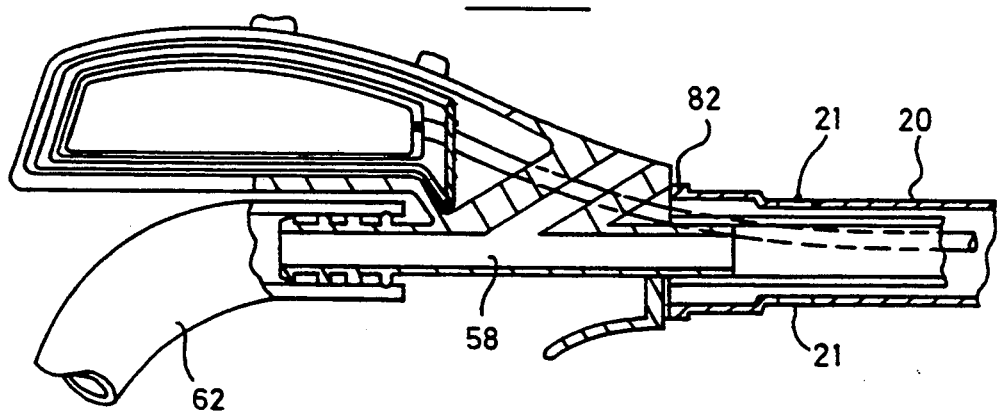
FIG. 3 is a section through the device shown in FIG. 2 in an assembled condition.
Figure 3:
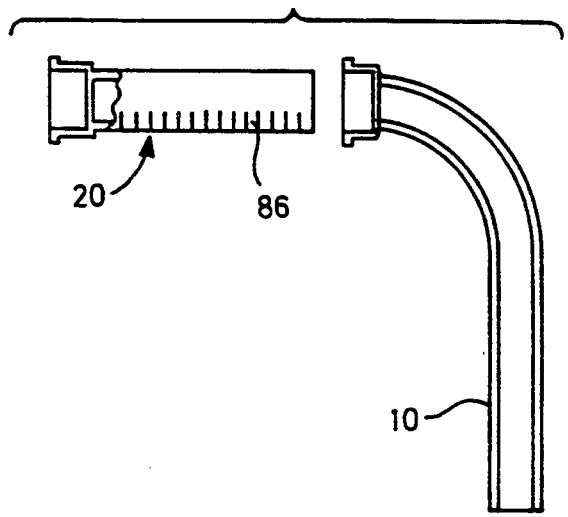

The catheter 16 is connected to the device 18 to control inflation of the membrane 28. As best seen in FIGS. 2 and 3, the lumen 24 is connected to a nipple 32 formed on a flexible bladder 34. The bladder 34 is integrally molded with bellows 36 to allow the volume of the bladder to vary and expel air through the nipple 32 as the volume is decreased.

The bladder 34 is located within an actuator assembly 38. The actuator assembly 38 includes a pair of wings 40,42 interconnected by a web 44. The connection between the wings 40,42 and the web 44 is in the form of a living hinge so that each of the wings 40,42 may pivot about its connection with the web 44 which also provides a resilience to bias the wings outwardly from one another. As best seen in FIG. 2, each of the wings 40,42 is formed as a hollow shell having upper and lower walls 46,48 and a peripheral wall 50. The cavity formed by the walls 46,48,50 provides a snug fit for the bladder 34 so that movement of the wings 40,42 toward one another causes a decrease in the volume of the bladder 34 to expel air through the nipple 32.

The actuator assembly 38 and bladder 34 are located within a frame 52 formed as a hoop-like band 54 with a downwardly extending flange 56. The band 54 is contoured to provide a comfortable fit within the hand of an operator as are the external surfaces of the wings 40,42.

The lumen 22 is connected to a passageway 58 integrally molded with the depending flange 56 and terminates in a ribbed nipple 60. The nipple 60 provides a convenient attachment point to a suction tube 62 shown in FIG. 3.

The flange 56 is also formed with a vent passage 64 that extends from the upper surface of the frame 52 to intersect the passage 58.

Figure 4:
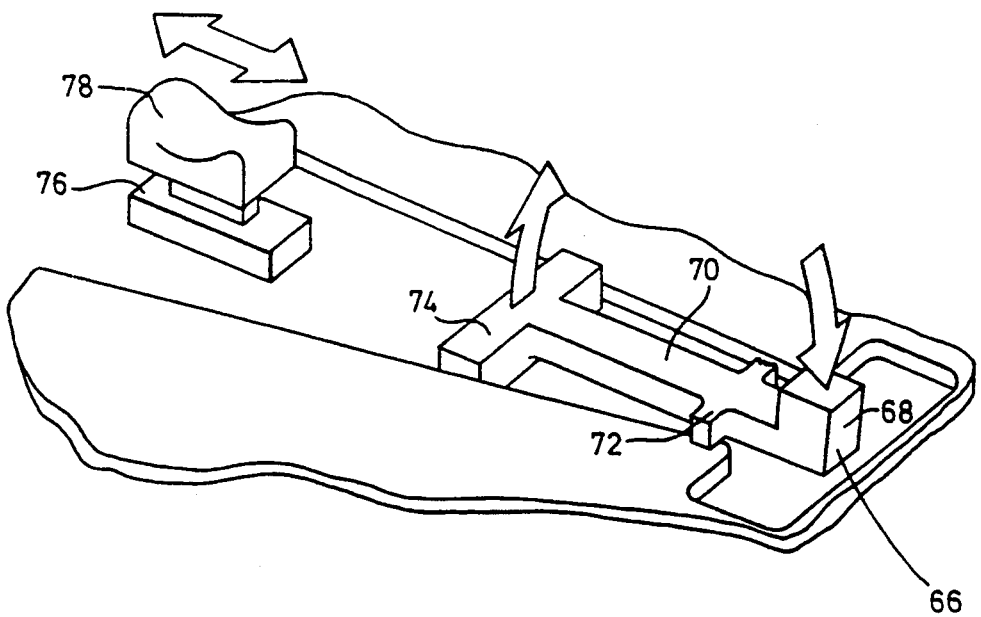
FIG. 4 is a perspective view of a portion of the device shown in FIG. 3.

The upper surface of the hoop 54 carries a latch assembly 66 shown in more detail in FIG. 4. The latch assembly includes an operating button 68 extending upwardly from a bar 70. The bar 70 is connected through lateral extensions 72 to the frame 52 to provide a resilient connection of the latch 66 to the frame 52 and bias the bar 70 into engagement with the wings 40,42. A transverse stop 74 is located at the end of the bar and is positioned to extend between the inwardly directed edges of the upper surfaces 46 of the wings 40,42. The bar 74 therefore maintains the wings 40,42 in spaced relationship and prevents movement of the wings toward one another.

A wedge 76 is also carried by the band 54 of frame 52 and is connected to a slider 78. Slider 78 is movable within an elongate slot 80 on the hoop 54 with a scale 81 being marked alongside the slot to correlate the position of the slider 78 with different diameters of tube 10. The wedge 76 may move in the slot 80 towards and away from the flange 56, that is toward and away from the pivot points of the wings 40,42 on the web 44.

The forwardly directed face of the flange 56 is provided with an abutment surface 82 against which the spacer 20 sits. The lumen 22 passes through an aperture 84 provided in the web 44 to one side of the frame 54 so as to emerge alongside the passageway 58 in the vicinity of the abutment face 82. The spacer 20 thus encompasses both the lumens 22,24.

As shown in FIG. 3, the spacer 20 is provided with a number of axially spaced indicia 86 which are correlated to the overall length of the tube 10 and the catheter 16. The tube 10 is provided in standard lengths, as is the catheter 16, with indications on the tube 10 and the catheter of this length. To avoid the catheter extending beyond the end of the tube 10, the spacer 20 should be adjusted to have an overall length equivalent to the difference between the catheter 16 and the tube 10. Spacer 20 is typically formed from a soft plastics material that may easily be cut to length with scissors. By using the indicia 86, the length of the tube can be selected to ensure that the catheter extends as close as possible to the bottom of the tube 10 without extending beyond it.

Spacer 20 may also be provided with two ports 21, one to provide a vent for the tube 10 as the catheter is inserted and withdrawn and the other to permit the insertion of a diluting solution, e.g. a saline solution, to facilitate removal of the secretions.

The operation of the device will now be described assuming that the tube 10 is to be cleaned using the catheter 16. The dual lumen catheter 16 attached to the inflation device 18 so that the lumen 24 is connected to the nipple 32 with the lumen 22 connected to the passageway 58. At this time, the latch 66 is engaged so that the bar 70 is in a position to prevent any movement of the wings 40,42. The slider 78 is moved to a location corresponding to the diameter of the tube 10.

The length of the spacer 20 is adjusted by cutting it at the appropriate indicia for the particular tube 10 and catheter 16. At that time, the suction tube 62 is connected to the opposite end of the passageway 58 but suction is not applied to the lumen 22 as air flows through the vent 64.

Figure 5:
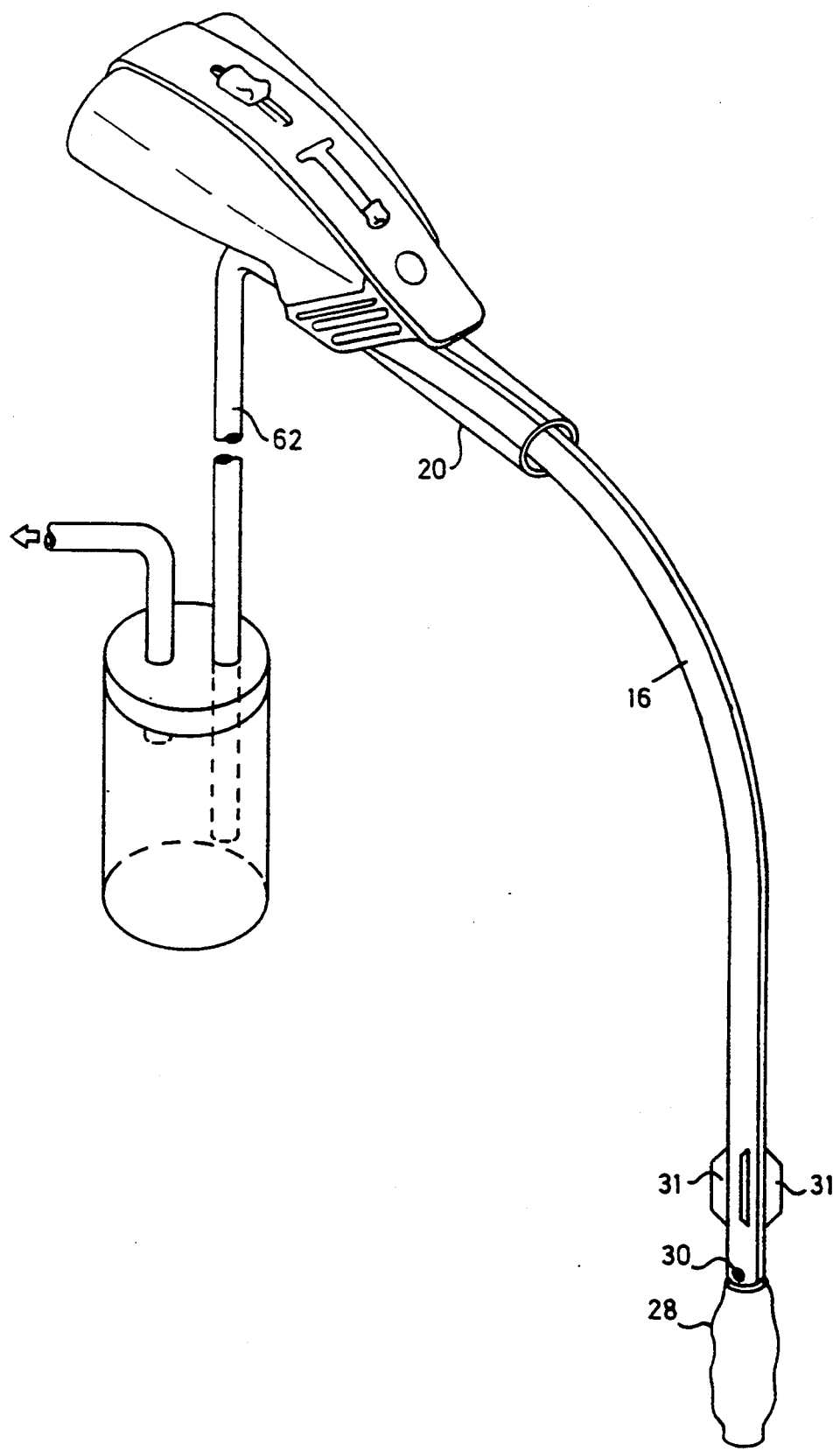
FIG. 5 is a view showing the device assembled and ready for use.
Figure 6B:
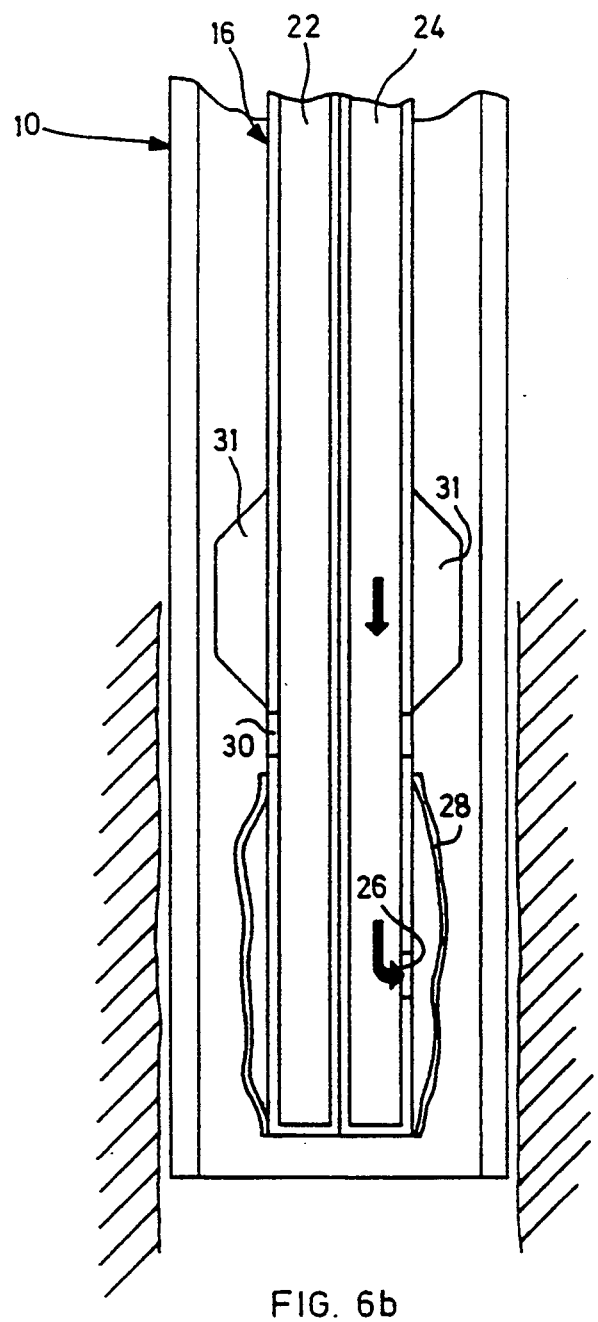

The catheter 16 is fed through the spacer 20 which is then connected to the inflation device 18 at the nipple 32. The assembled catheter and inflation device as shown in FIG. 5 is then inserted into the tube 10 after disconnection from the ventilator with the membrane in a deflated condition as shown in FIG. 6b. The catheter is inserted until such time as the spacer 20 abuts the end of the tube 10, indicating that the tip of the catheter 16 is adjacent the bottom of the tube 10. At this time, the latch 66 has not been released and so any manipulation of the device 18 during insertion will not move the wings 40,42 and cause inadvertent inflation of the membrane 28.

With the catheter 16 in place, the button 68 is depressed to cause the bar 70 to pivot about the lateral extension 72 and move the transverse stop 74 out of engagement with the wings 40,42. The wings may now be pivoted toward one another about their connections with the web 44, causing a reduction in the volume of the bladder 34. This causes air to be expelled through the nipple 32 into the lumen 24 to inflate the membrane 28 and bring it into engagement with the walls of the tube 10.

The wedge 76 acts as an abutment for the wings 40,42 so that their movement toward one another is limited. Over-inflation of the membrane 28 is thus prevented but at the same time the operator is confident that the membrane has engaged the walls of the tube 10. The scale 81 is chosen such that the volume of air to be expelled from the bladder is sufficient to inflate the membrane 28 and place it in wiping contact with the wall without causing it to engage the wall of the tube 10 so firmly that it binds and will not slide.

The catheter may now be withdrawn wiping the surfaces of the tube 10 at the same time. As the catheter 16 is withdrawn, suction is selectively applied by covering and uncovering the vent passage 64 with the thumb of the operator. It will be noted that during removal of the catheter, the forces exerted on the wings 40,42 will not cause any further expulsion of air from the bladder 34 because of the abutment against the wedge 76. The catheter 16 continues to be removed until such time as the membrane 28 leaves the tube 10 and enters the spacer 20. The spacer 20 can then be disconnected and the ventilator replaced on the tube 10.

The device 18 therefore provides for controlled inflation of the membrane 28 by virtue of the wedge 76 and unintentional inflation of the catheter is avoided by the latch 66. This ensures that as the catheter is inserted it does not dislodge any of the secretions in the tube 10.

In the event that the catheter has to be deflated during removal, it is simply necessary to release the wings 40,42 which will resume their normal freebody position. In that position, the resilient connections provided by lateral extension 72 of the latch 66 moves the bar 74 back into a locking position so that further inadvertent expulsion of the air from the bladder 34 is avoided.

Although the invention has been described with reference to the cleaning of an ETT, it will be appreciated that it has applicability in the insertion of catheters into other body cavities or tubes to perform similar functions or other procedures. The controlled environment provided by the tube 10 in terms of length and diameter facilitates the control of the inflation of the catheter, allowing the wedge 76 to be accurately located, but the benefits of inhibiting inflation of the catheter and selectively applying the suction to the second lumen may have advantages in other procedures.

We claim:

1. A device to control the inflation of a balloon catheter comprising;
   a support frame;
   a flexible bladder located within said support frame and having an outlet for connection to a lumen of a balloon catheter;
   an actuator mounted on said frame and operable upon and movable relative to said bladder to decrease the volume of and expel fluid from the bladder to inflate said balloon catheter;
   a releasable latch means for operating upon said actuator to hold said actuator in a latched position and thereby inhibit movement of the actuator in a direction to decrease the volume of the bladder and thereby prevent inflation of the balloon catheter; and
   an abutment means operable upon release of said latch means for limiting movement of the actuator from said latched position in a direction to decrease the volume of the bladder to thereby limit the change in the volume of the bladder, said abutment means being adjustable relative to said latched position of the actuator to vary the volume of fluid expelled in moving said actuator between said latched position and said abutment means to inflate said catheter may be varied.

2. A device according to claim 1 wherein said frame is formed as an open loop configured to fit within a hand and said bladder is located within said loop.

3. A device according to claim 2 wherein said actuator includes a pair of rigid wings disposed on opposite sides of said frame and movable toward one another to engage said bladder.

4. A device according to claim 3 wherein said latch means is mounted on said frame and is engageable with each of said wings to prevent relative movement therebetween.

5. A device according to claim 4 wherein said wings are pivotally interconnected toward one end of said frame and said abutment means is movable on the frame toward and away from said one end to vary the angular disposition at which said wings engage said abutment means.

6. A device according to claim 5 wherein each wing is pivotally mounted to opposite ends of a web located within said frame and said bladder includes a nipple projecting outwardly from the bladder and through said spacer for connection to said catheter.

7. A device according to claim 6 wherein said nipple projects to one side of said frame.

8. A device according to claim 7 wherein said wall means defining said passage extends beneath said frame and is secured thereto.

9. A device according to claim 4 wherein said latch means is biased to a position in which it engages said wings.

10. A device according to claim 1 wherein said latch means is movably mounted on said frame and engages said actuator to inhibit relative movement therebetween.

11. A device according to claim 10 wherein said actuator is mounted for pivotal movement relative to the frame axis and said abutment means is movable toward and away from the pivot axis to vary the limit of movement of the actuator relative to the frame.

12. A device according to claim 11 wherein the vent is formed in the frame.

13. A device according to claim 1 including a tubular spacer interconnecting said frame with said catheter, said catheter passing therethrough, said spacer being adapted to extend to a tube into which said catheter is to be inserted to limit movement of the frame toward the tube.

14. A device according to claim 13 wherein said spacer is adjustable in length and has axially spaced indicia thereon correlated to the length of the catheter and tube to indicate the limit of movement of the frame relative to the tube.

15. A device according to claim 14 wherein said spacer is formed from a soft plastics material that may be readily cut to adjust the length thereof.

16. A device according to claim 1 including wall means supported by said support frame for movement therewith and defining a passage having an outlet for connection to a further lumen of the catheter to apply suction thereto.

17. A device according to claim 16 including a vent connected to the passage to allow air to flow to the passage and to prevent suction from being generated in said further lumen.

* * * * *